US00PP26331P3

(12) United States Plant Patent
Klemm et al.

(10) Patent No.: US PP26,331 P3
(45) Date of Patent: Jan. 19, 2016

(54) ***PELARGONIUM* PLANT NAMED 'KLEIZ13338'**

(50) Latin Name: ***Pelargonium* sp.**
Varietal Denomination: KLEIZ13338

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 119 days.

(21) Appl. No.: 13/998,657

(22) Filed: Nov. 20, 2013

(65) Prior Publication Data

US 2015/0143597 P1 May 21, 2015

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Keith Robinson
(74) *Attorney, Agent, or Firm* — James M. Weatherly; Bethany R. Roahrig; Cochran Freund & Young, LLC

(57) ABSTRACT

A new *Pelargonium* plant particularly distinguished by having semi-double flowers with a white color, compact growth habit and strong branching, is disclosed.

1 Drawing Sheet

Genus and species: *Pelargonium* sp.
Variety denomination: 'KLEIZ13338'.

BACKGROUND OF THE NEW PLANT

The present invention comprises a new and distinct variety of *Pelargonium*, botanically known as *Pelargonium* sp. and hereinafter referred to by the variety name 'KLEIZ13338'. 'KLEIZ13338' originated from a controlled cross between the female *Pelargonium* variety 'Cassandra' (U.S. Plant Pat. No. 6,220), having white flowers with medium branching and a strong growth habit, and the proprietary male *Pelargonium* variety 'PP 06 086' (unpatented), having orange flowers, with small branching and a small growth habit.

In June 2008 the two *Pelargonium* parental lines 'Cassandra' and 'PP 06 086' were crossed in Stuttgart, Germany and seeds were obtained. The seeds were sown and plants were grown for evaluation. A plant line was selected in June 2009 and named 'KLEIZ13338'. In June 2009 'KLEIZ13338' was first vegetatively propagated by vegetative cuttings. 'KLEIZ13338' was found to reproduce true to type in successive generations of asexual propagation via vegetative cuttings in Stuttgart, Germany.

CROSS REFERENCE TO RELATED APPLICATIONS

Plant Breeder's Rights for 'KLEIZ13338' were applied for in Canada on Feb. 8, 2013, Application No. 13-7923. 'KLEIZ13338' has not been made publicly available or sold more than one year prior to the filing date of this application.

SUMMARY

The following are the most outstanding and distinguishing characteristics of this new variety when grown under normal horticultural practices in Stuttgart, Germany.

1. White flower color;
2. Semi-double flowers;
3. Compact growth habit; and
4. Strong branching.

DESCRIPTION OF THE PHOTOGRAPH

This new *Pelargonium* plant is illustrated by the accompanying photograph which shows an overall view of the plant. The photograph is of a 4 to 5 month-old plant grown in Stuttgart, Germany under greenhouse conditions in May 2012.

The colors shown are as true as can be reasonably obtained by conventional photographic procedures.

DESCRIPTION OF THE NEW VARIETY

The following detailed descriptions set forth the distinctive characteristics of 'KLEIZ13338'. The data which define these characteristics were collected from asexual reproductions carried out in Stuttgart, Germany. Data was collected on fifteen-week-old plants grown in an indoor trial in Stuttgart, Germany under greenhouse conditions in April 2013. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium* sp.
- *Common.*—*Pelargonium.*
- *Designation.*—'KLEIZ13338'.

Parentage:
- *Female parent.*—*Pelargonium* line 'Cassandra' (U.S. Plant Pat. No. 6,220).
- *Male parent.*—*Pelargonium* line 'PP 06 086' (unpatented).

Plant:
- *Habit.*—Upright.
- *Height.*—20.0 cm.
- *Spread.*—20.0 cm.

*Life cycle*.—Annual, January to April in a greenhouse, May to October outside.
*Form*.—Rounded, potted plant.
*Time to produce a rooted cutting*.—18 days.
*Time to bloom from propagation*.—75 days.
*Lastingness of inflorescence on the plant*.—About 2 weeks.
*Root type*.—Medium, freely branching.
*Color*.—White.

Stems:
*Color*.—RHS 137C.
*Quantity*.—4 to 8 branches.
*Texture*.—Little short pubescence.
*Pubescence*.—Present.
*Stem form*.—Round.
*Diameter*.—0.6 cm.
*Length*.—8.0 cm to 12.0 cm.
*Internode length*.—1.5 cm to 2.0 cm.
*Anthocyanin*.—Absent.

Leaves:
*Arrangement*.—Alternate.
*Shape*.—Round, ivy shaped.
*Apex*.—Obtuse.
*Base*.—Open.
*Margin*.—Crenate.
*Surface Texture*.—Upper surface: Rough. Lower surface: Smooth.
*Length*.—5.0 cm.
*Width*.—6.0 cm.
*Color*.—Upper surface: RHS 137A. Lower surface: RHS 137D.
*Surface pubescence*.—Upper surface: Sparse. Lower surface: Absent.
*Petiole*.—Length: 5.0 cm to 7.0 cm. Diameter: 0.12 cm. Strength: Medium. Color: RHS 137C.
*Venation pattern*.—Palmate.
*Venation color*.—Upper surface: RHS 138A. Lower surface: RHS 138B.

Inflorescence:
*Umbels*.—Shape: Round. Length: 5.0 cm to 6.0 cm. Diameter: 8.0 cm.
*Individual florets of the umbel*.—Depth 1.0 cm. Diameter: 3.5 cm. Lastingness of individual flowers: About 6 to 8 days.
*Fragrance*.—Absent.
*Number of inflorescences per plant*.—7 to 9.

Flower buds:
*Cluster shape*.—Round.
*Cluster size*.—Length: 2.0 cm. Width: 2.0 cm.
*Texture*.—Rough.
*Bud*.—Length: 0.7 cm to 0.9 cm. Width: 0.6 cm. Shape: Elliptic, ovate. Apex: Cuspidate. Base: Obtuse. Margin: Smooth. Color: RHS 138A.

Petals:
*Quantity per flower*.—5.
*Shape*.—Ovate.
*Apex*.—Smooth, round.
*Base*.—Obtuse.
*Margin*.—Entire.
*Length*.—2.0 cm.
*Width*.—1.0 cm.
*Texture* (*both surfaces*).—Smooth.
*Color of lobes*.—Upper and lower lobes: Upper surface: RHS 157B. Lower surface: RHS 157C.

Sepals:
*Number per flower*.—5.
*Shape*.—Elliptic to ovate.
*Apex*.—Acute.
*Base*.—Obtuse.
*Margin*.—Entire.
*Texture* (*both surfaces*).—Smooth.
*Color*.—Upper surface: RHS 138B. Lower surface: RHS 138D.
*Length*.—0.9 cm.
*Width*.—0.4 cm.

Pedicel:
*Length*.—0.5 cm to 1.2 cm.
*Diameter*.—0.15 cm.
*Color*.—RHS 138D.
*Texture*.—Light short pubescence (a little rough).
*Strength*.—Medium.

Peduncle:
*Length*.—10.0 cm to 15.0 cm.
*Diameter*.—0.5 cm.
*Color*.—RHS 137D.
*Texture*.—Rough.
*Strength*.—Medium.

Reproductive organs:
*Stamens*.—Number: Mostly 5. Anther length: 0.2 cm Anther color: RHS N155C. Filament length: 0.6 cm. Filament color: RHS N155B. Pollen amount: Moderate. Pollen color: RHS 25D.
*Pistils*.—Number: 1. Stigma color: RHS 68C. Style length: 0.1 cm. Style color: RHS 56D. Ovary arrangement: Erect. Ovary color: RHS 142D. Ovary length: 0.4 cm. Ovary diameter: 0.1 cm.

Fruit and seed set: None observed.
Disease and pest/insect resistance: None observed.

COMPARISON WITH PARENTAL LINES AND KNOWN VARIETY

'KLEIZ13338' is a distinct variety of *Pelargonium* having violet ray florets and dark green leaves; 'KLEIZ13338' is distinguished from its parents as described in Table 1:

TABLE 1

Comparison with Parental Lines

| Trait | 'KLEIZ13338' | Female parent 'Cassandra' | Male Parent 'PP 06 086' |
|---|---|---|---|
| Growth habit | Compact | Strong | Small |
| Flower color | White | White | Orange |
| Branching | Strong | Medium | Small, little |

'KLEIZ13338' is most similar to the commercial *Pelargonium* plant named 'Cassandra' (U.S. Plant Pat. No. 6,220). Differences between the two varieties are described in Table 2:

TABLE 2

Comparison with Similar Variety

| Trait | 'KLEIZ13338' | Commercial line 'Cassandra' |
|---|---|---|
| Flower fullness | Semi double flowers | Double flowers |
| Growth habit | Compact | Strong |

We claim:

1. A new and distinct variety of *Pelargonium* plant named 'KLEIZ13338' as illustrated and described herein.

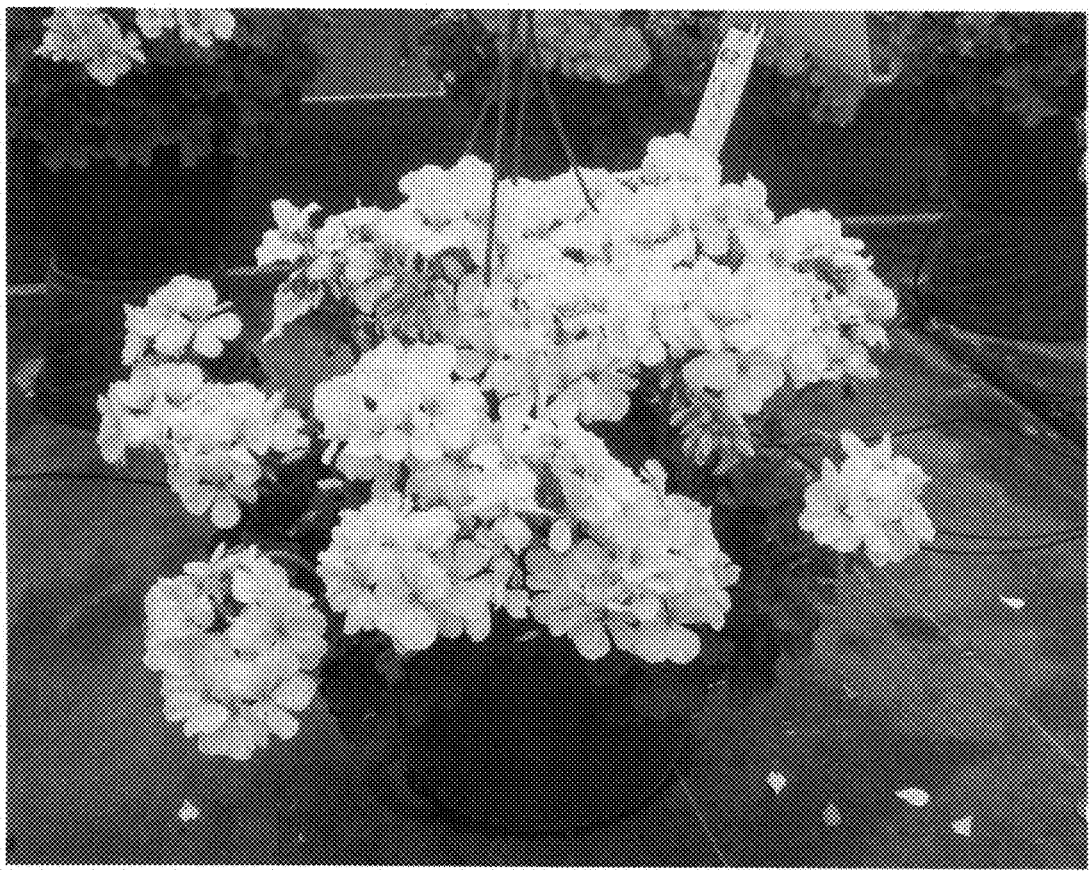

* * * * *